(12) United States Patent
McAnally et al.

(10) Patent No.: US 10,168,264 B2
(45) Date of Patent: Jan. 1, 2019

(54) METHOD OF GENERATING A DRIVE SIGNAL FOR A VIBRATORY SENSOR

(71) Applicant: Micro Motion, Inc., Boulder, CO (US)

(72) Inventors: Craig B McAnally, Thornton, CO (US); Andrew S. Kravitz, Frederick, CO (US)

(73) Assignee: Micro Motion, Inc., Boulder, CO (US)

( * ) Notice: Subject to any disclaimer, the term of this patent is extended or adjusted under 35 U.S.C. 154(b) by 228 days.

(21) Appl. No.: 14/781,259

(22) PCT Filed: Apr. 18, 2014

(86) PCT No.: PCT/US2014/034610
§ 371 (c)(1),
(2) Date: Sep. 29, 2015

(87) PCT Pub. No.: WO2014/176122
PCT Pub. Date: Oct. 30, 2014

(65) Prior Publication Data
US 2016/0054212 A1     Feb. 25, 2016

Related U.S. Application Data

(60) Provisional application No. 61/815,139, filed on Apr. 23, 2013.

(51) Int. Cl.
| | | |
|---|---|---|
| *G01N 9/00* | (2006.01) |
| *G01F 1/84* | (2006.01) |
| *G01N 9/34* | (2006.01) |
| *G01N 11/16* | (2006.01) |
| *G01F 23/296* | (2006.01) |

(52) U.S. Cl.
CPC ........... *G01N 9/002* (2013.01); *G01F 1/8431* (2013.01); *G01F 1/8436* (2013.01); *G01F 23/2967* (2013.01); *G01N 9/34* (2013.01); *G01N 11/16* (2013.01); *G01N 2009/006* (2013.01)

(58) Field of Classification Search
None
See application file for complete search history.

(56) References Cited

U.S. PATENT DOCUMENTS

| | | |
|---|---|---|
| 4,007,627 A | 2/1977 | Stansfeld |
| 4,738,144 A | 4/1988 | Cage |
| (Continued) | | |

FOREIGN PATENT DOCUMENTS

| | | |
|---|---|---|
| CN | 102506951 A | 6/2012 |
| GB | 2236591 A | 4/1991 |
| (Continued) | | |

*Primary Examiner* — Paul West
*Assistant Examiner* — Mark A Shabman
(74) *Attorney, Agent, or Firm* — The Ollila Law Group LLC (57) ABSTRACT

A method (600) of generating a drive signal for a vibratory sensor (5) is provided. The method (600) includes vibrating a vibratory element (104, 510) configured to provide a vibration signal, receiving the vibration signal from the vibratory element (104, 510) with a receiver circuit (134), generating a drive signal that vibrates the vibratory element (104, 510) with a driver circuit (138) coupled to the receiver circuit (134) and the vibratory element (104, 510), and comparing a phase of the generated drive signal with a phase of the vibration signal.

18 Claims, 6 Drawing Sheets

(56) References Cited

U.S. PATENT DOCUMENTS

| | | | |
|---|---|---|---|
| 4,801,897 A | | 1/1989 | Flecken |
| 4,841,256 A | | 6/1989 | Gastgeb |
| 4,965,532 A | | 10/1990 | Sakurai |
| 5,613,009 A | * | 3/1997 | Miyazaki ............... F16F 7/1011 |
| | | | 381/71.11 |
| 5,895,848 A | | 4/1999 | Wilson et al. |
| 2002/0040592 A1 | | 4/2002 | Getman et al. |
| 2004/0173031 A1 | | 9/2004 | Gicza |
| 2008/0184813 A1 | | 8/2008 | Patten et al. |
| 2008/0252283 A1 | | 10/2008 | McAnally et al. |
| 2009/0205411 A1 | | 8/2009 | Mueller |
| 2010/0083750 A1 | * | 4/2010 | D'Angelico ........ G01F 23/2967 |
| | | | 73/290 V |
| 2010/0083752 A1 | | 4/2010 | Malinek |
| 2010/0161251 A1 | * | 6/2010 | D'Angelico ........ G01F 23/2967 |
| | | | 702/54 |
| 2012/0046765 A1 | * | 2/2012 | Nikolic ................ B06B 1/0253 |
| | | | 700/90 |

FOREIGN PATENT DOCUMENTS

| | | | |
|---|---|---|---|
| JP | 2004511771 A | | 4/2004 |
| JP | 2008-536111 A | | 9/2008 |
| RU | 2460974 C2 | | 9/2012 |
| WO | 9726512 A1 | | 7/1997 |
| WO | 0101083 A1 | | 1/2001 |
| WO | 2006104485 A1 | | 10/2006 |
| WO | 2007047524 A2 | | 4/2007 |
| WO | 2013009307 A1 | | 1/2013 |

* cited by examiner

METHOD OF GENERATING A DRIVE SIGNAL FOR A VIBRATORY SENSOR

TECHNICAL FIELD

The embodiments described below relate to vibratory sensors and, more particularly, to methods of generating a drive signal for a vibratory sensor.

BACKGROUND

Vibratory sensors, such as vibratory densitometers and vibratory viscometers, operate by detecting motion of a vibrating element that vibrates in the presence of a fluid to be characterized. Properties associated with the fluid, such as density, viscosity, temperature and the like, can be determined by processing a vibration signal or signals received from one or more motion transducers associated with the vibrating element. The vibration of the vibrating element is generally affected by the combined mass, stiffness, and damping characteristics of the vibrating element in combination with the fluid.

Figure 1:
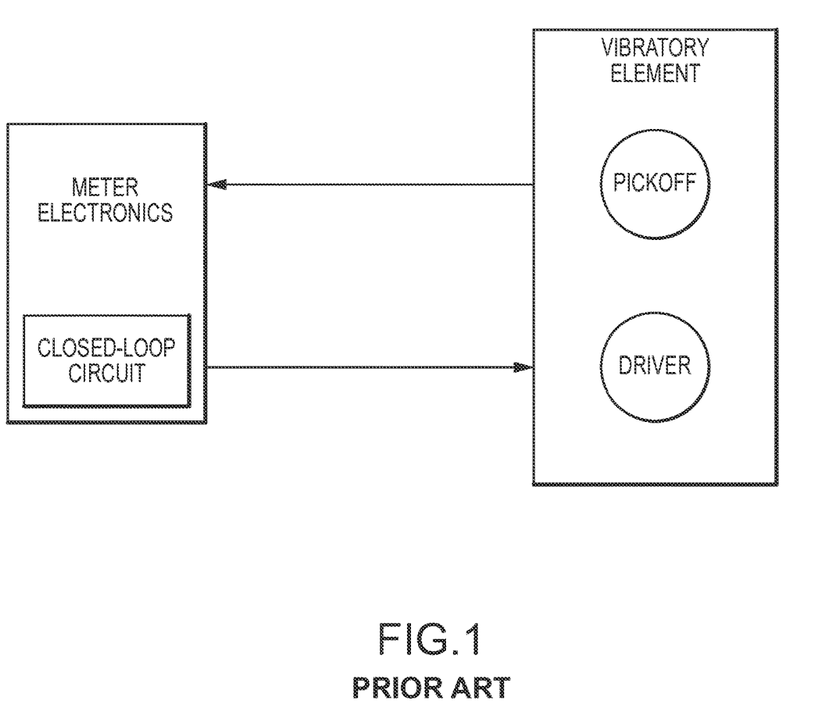
FIG. 1 shows a prior art vibratory sensor comprising a vibratory element and meter electronics coupled to the vibratory element.

FIG. 1 shows a prior art vibratory sensor comprising a vibratory element and meter electronics coupled to the vibratory element. The prior art vibratory sensor includes a driver for vibrating the vibratory element and a pickoff that creates a vibration signal in response to the vibration. The vibration signal is a continuous time or analog signal. The meter electronics receives the vibration signal and processes the vibration signal to generate one or more fluid characteristics or fluid measurements. The meter electronics determines both the frequency and the amplitude of the vibration signal. The frequency and amplitude of the vibration signal can be further processed to determine a density of the fluid.

The prior art vibratory sensor provides a drive signal for the driver using a closed-loop circuit. The drive signal is typically based on the received vibration signal. The prior art closed-loop circuit modifies or incorporates the vibration signal or parameters of the vibration signal into the drive signal. For example, the drive signal may be an amplified, modulated, or an otherwise modified version of the received vibration signal. The received vibration signal can therefore comprise a feedback that enables the closed-loop circuit to achieve a target frequency. Using the feedback, the closed-loop circuit incrementally changes the drive frequency and monitors the vibration signal until the target frequency is reached.

The target frequency of the fluid can be correlated with the desired phase difference between the drive signal and the vibration signal. Fluid properties, such as the viscosity and density of the fluid, can be determined from the frequencies where the phase difference between the drive signal and the vibration signal is 135° and 45°. These desired phase differences, denoted as first phase difference φ1 and second phase difference φ2, can correspond to the half power or 3 dB frequencies. A first target frequency φ1 is defined as a frequency where the first phase difference φ1 is 135°. The second target frequency ω2 is defined as a frequency where the second phase difference φ2 is 45°. Density measurements made at the second target frequency ω2, can be independent of fluid viscosity. Accordingly, density measurements made where the second phase difference φ2 is 45° can be more accurate than density measurements made at other phase differences.

The closed-loop approach typically measures the frequency of the vibration signal to determine how much to shift the drive signal frequency to achieve the second phase difference φ2. Using the measured frequency, a relationship between the measured frequency and the phase is used to determine if there is a phase difference of 45° between the drive signal and the vibration signal. However, the closed-loop approach to measuring fluid properties has some associated issues. For example, the frequency of the vibration signal must first be measured to obtain a desired phase difference between the vibration signal and the drive signal. This can be problematic because the vibration signal can be very small relative to noise. As a result, measuring the frequency from the vibration signal requires filtering. This filtering can cause delays in the frequency measurement, which can cause instability in drive control algorithms. Additionally, any unfiltered noise in the vibration signal will be reproduced in the drive signal. Noise in the drive signal can cause drive instability as well as inaccuracies in the frequency measurement.

Accordingly, there is a need for a method for generating a drive signal for a vibratory sensor that does not require the frequency measurements associated with the closed-loop approach.

SUMMARY

A method of generating a drive signal for a vibratory sensor is provided. According to an embodiment, the method comprises vibrating a vibratory element configured to provide a vibration signal, receiving the vibration signal from the vibratory element with a receiver circuit. The method further comprises generating the drive signal that vibrates the vibratory element with a driver circuit coupled to the receiver circuit and the vibratory element, and comparing a phase of the generated drive signal with a phase of the vibration signal.

A vibratory sensor is provided. According to an embodiment, the vibratory sensor comprises a vibratory element configured to provide a vibration signal, a receiver circuit that receives the vibration signal from the vibratory element, and a driver circuit coupled to the receiver circuit and the vibratory element. The driver circuit is configured to generate a drive signal that vibrates the vibratory element, and compare a phase of the generated drive signal with a phase of the vibration signal.

ASPECTS

According to an aspect, a method (600) of generating a drive signal for a vibratory sensor (5) comprises vibrating a vibratory element (104, 510) configured to provide a vibration signal, receiving the vibration signal from the vibratory element (104, 510) with a receiver circuit (134), generating the drive signal that vibrates the vibratory element (104, 510) with a driver circuit (138) coupled to the receiver circuit (134) and the vibratory element (104, 510), and comparing a phase of the generated drive signal with a phase of the vibration signal.

Preferably, the comparing the phase of the generated drive signal with the phase of the vibration signal comprises comparing a sampled generated drive signal with a sampled vibration signal.

Preferably, the method (600) further comprises removing at least one frequency component from the at least one of the sampled generated drive signal and the sampled vibration signal.

Preferably, the comparing the sampled generated drive signal with the sampled vibration signal comprises performing a correlation of the sampled generated drive signal and the sampled vibration signal.

Preferably, the comparing the sampled generated drive signal with the sampled vibration signal comprises conjugating one of the sampled generated drive signal and the sampled vibration signal, and multiplying the conjugated one of the sampled generated drive signal and the sampled vibration signal with the non-conjugated one of the sampled generated drive signal and the sampled vibration signal.

Preferably, the comparing the phase of the generated drive signal with the phase of the vibration signal comprises determining a measured phase difference $\phi_m$ between the phase of the generated drive signal and the phase of the vibration signal, and comparing the measured phase difference $\phi_m$ with a target phase difference $\phi_t$ to determine if the measured phase difference $\phi_m$ is at the target phase difference $\phi_t$.

Preferably, the method (600) further comprises measuring a density of a fluid when the measured phase difference $\phi_m$ is at the target phase difference $\phi_t$.

Preferably, the method (600) further comprises determining a command frequency ω from the comparison of the phase of the generated drive signal and the phase of the vibration signal, providing the command frequency ω to a signal generator (147c), and generating the drive signal at the command frequency ω with the signal generator (147c).

Preferably, the method (600), wherein the generating the drive signal at the command frequency ω with the signal generator (147c) comprises forming a synthesized drive signal with a drive synthesizer (544), and converting the synthesized drive signal to the generated drive signal with a digital to analog converter (534).

According to an aspect, a vibratory sensor (5) comprises a vibratory element (104, 510) configured to provide a vibration signal, a receiver circuit (134) that receives the vibration signal from the vibratory element (104), and a driver circuit (138) coupled to the receiver circuit (134) and the vibratory element (104), the driver circuit (138) configured to generate a drive signal that vibrates the vibratory element (104, 510), and compare a phase of the generated drive signal with a phase of the vibration signal.

Preferably, the driver circuit (138) being configured to compare a sampled generated drive signal with a sampled vibration signal.

Preferably, the driver circuit (138) is further configured to remove at least one frequency component from at least one of the sampled generated drive signal and the sampled vibration signal.

Preferably, the driver circuit (138) is further configured to perform a correlation of the sampled generated drive signal and the sampled vibration signal.

Preferably, the driver circuit (138) is further configured to conjugate one of the sampled generated drive signal and the sampled vibration signal, and multiplies the conjugated one of the sampled generated drive signal and the sampled vibration signal with the non-conjugated one of the sampled generated drive signal and the sampled vibration signal.

Preferably, the driver circuit (138) is comprised of a phase detector (147b, 542) configured to determine a measured phase difference $\phi_m$ between the phase of the generated drive signal and the phase of the vibration signal, and compare the measured phase difference $\phi_m$ with a target phase difference $\phi_t$ to determine if the measured phase difference $\phi_m$ is at the target phase difference $\phi_t$.

Preferably, the driver circuit (138) is further configured to measure the density of the fluid when the measured phase difference $\phi_m$ is at the target phase difference $\phi_t$.

Preferably, the driver circuit (138) is comprised of a phase detector (147b, 542) and a signal generator (147c) wherein the phase detector (147b) is configured to determine a command frequency ω from the comparison of the phase of the generated drive signal and the phase of the vibration signal and provides the command frequency ω to a signal generator (147c); and the signal generator (147c) configured to generate the drive signal at the command frequency ω.

Preferably, the signal generator (147c) comprises a drive synthesizer (544) configured to form a synthesized drive signal, and a digital to analog converter (534) configured to convert the synthesized drive signal to the generated drive signal.

BRIEF DESCRIPTION OF THE DRAWINGS

The same reference number represents the same element on all drawings. It should be understood that the drawings are not necessarily to scale.

DETAILED DESCRIPTION

FIGS. 2-6 and the following description depict specific examples to teach those skilled in the art how to make and use the best mode of embodiments of a method for generating a drive signal for a vibratory sensor. For the purpose of teaching inventive principles, some conventional aspects have been simplified or omitted. Those skilled in the art will appreciate variations from these examples that fall within the scope of the present description. Those skilled in the art will appreciate that the features described below can be combined in various ways to form multiple variations of the method for generating the drive signal for the vibratory sensor. As a result, the embodiments described below are not limited to the specific examples described below, but only by the claims and their equivalents.

Figure 2:
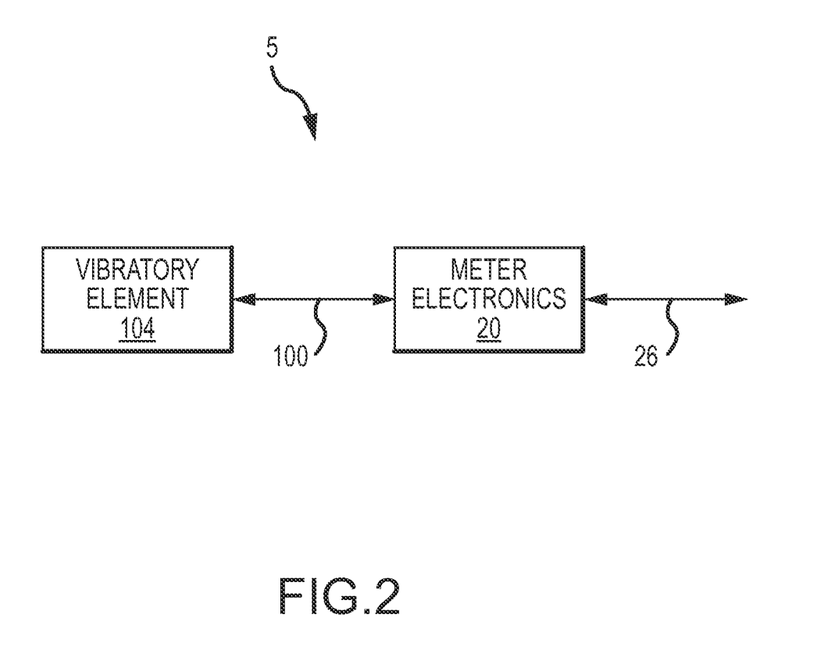
FIG. 2 shows a vibratory sensor 5 according to an embodiment.

FIG. 2 shows a vibratory sensor 5 according to an embodiment. The vibratory sensor 5 may comprise a vibratory element 104 and meter electronics 20, wherein the vibratory element 104 is coupled to the meter electronics 20 by a lead or leads 100. In some embodiments, the vibratory sensor 5 may comprise a vibratory tine sensor or fork density sensor (see FIG. 3 and the accompanying discussion). However, other vibratory sensors are contemplated and are within the scope of the description and claims.

The vibratory sensor 5 may be at least partially immersed into a fluid to be characterized. The fluid can comprise a liquid or a gas. Alternatively, the fluid can comprise a multi-phase fluid, such as a liquid that includes entrained gas, entrained solids, multiple liquids, or combinations thereof. Some exemplary fluids include cement slurries, petroleum products, or the like. The vibratory sensor 5 may be mounted in a pipe or conduit, a tank, a container, or other fluid vessels. The vibratory sensor 5 can also be mounted in a manifold or similar structure for directing a fluid flow.

However, other mounting arrangements are contemplated and are within the scope of the description and claims.

The vibratory sensor 5 operates to provide fluid measurements. The vibratory sensor 5 may provide fluid measurements including one or more of a fluid density and a fluid viscosity for a fluid, including flowing or non-flowing fluids. The vibratory sensor 5 may provide fluid measurements including a fluid mass flow rate, a fluid volume flow rate, and/or a fluid temperature. This listing is not exhaustive and the vibratory sensor 5 may measure or determine other fluid characteristics.

The meter electronics 20 can provide electrical power to the vibratory element 104 via the lead or leads 100. The meter electronics 20 controls operation of the vibratory element 104 via the lead or leads 100. For example, the meter electronics 20 may generate a drive signal and provide the generated drive signal to the vibratory element 104, wherein the vibratory element 104 generates a vibration in one or more vibratory components using the generated drive signal. The generated drive signal can control the vibrational amplitude and frequency of the vibratory element 104. The generated drive signal can also control the vibrational duration and/or vibrational timing.

The meter electronics 20 can also receive a vibration signal or signals from the vibratory element 104 via the lead or leads 100. The meter electronics 20 may process the vibration signal or signals to generate a density measurement, for example. The meter electronics 20 processes the vibration signal or signals received from the vibratory element 104 to determine a frequency of the signal or signals. Further, or in addition, the meter electronics 20 processes the vibration signal or signals to determine other characteristics of the fluid, such as a viscosity or a phase shift between signals, that can be processed to determine a fluid flow rate, for example. Other vibrational response characteristics and/or fluid measurements are contemplated and are within the scope of the description and claims.

The meter electronics 20 can be further coupled to a communication link 26. The meter electronics 20 may communicate the vibration signal over the communication link 26. The meter electronics 20 may also process the received vibration signal to generate a measurement value or values and may communicate the measurement value or values over the communication link 26. In addition, the meter electronics 20 can receive information over the communication link 26. For example, the meter electronics 20 may receive commands, updates, operational values or operational value changes, and/or programming updates or changes over the communication link 26.

Figure 3:
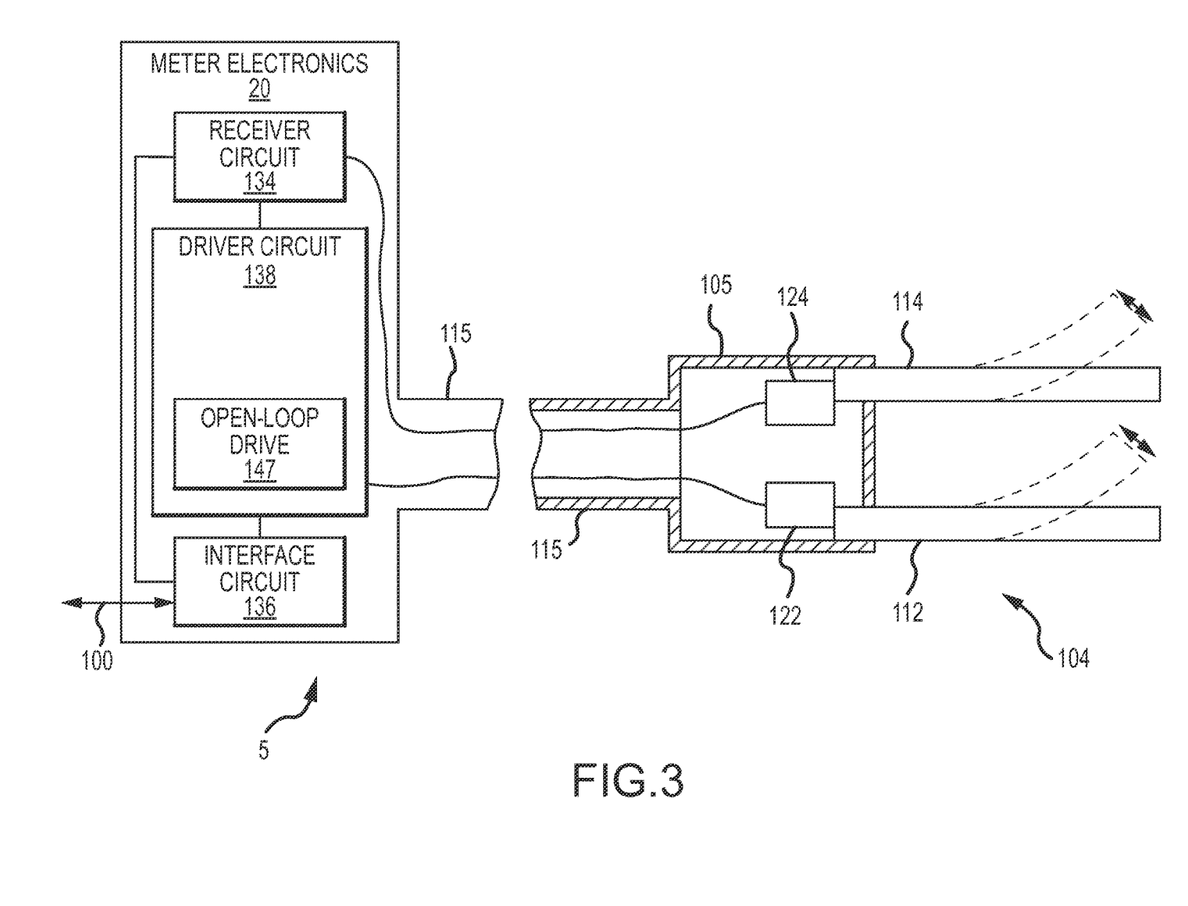
FIG. 3 shows the vibratory sensor 5 according to an embodiment.

FIG. 3 shows the vibratory sensor 5 according to an embodiment. The meter electronics 20 is coupled to the vibratory element 104 by a shaft 115 in the embodiment shown. The shaft 115 may be of any desired length. The shaft 115 may be at least partially hollow. Wires or other conductors may extend between the meter electronics 20 and the vibratory element 104 through the shaft 115. The meter electronics 20 includes circuit components such as a receiver circuit 134, an interface circuit 136, and a driver circuit 138. In the embodiment shown, the receiver circuit 134 and the driver circuit 138 are directly coupled to the leads of the vibratory element 104. Alternatively, the meter electronics 20 can comprise a separate component or device from the vibratory element 104, wherein the receiver circuit 134 and the driver circuit 138 are coupled to the vibratory element 104 via the lead or leads 100.

In the embodiment shown, the vibratory element 104 of the vibratory sensor 5 comprises a tuning fork structure, wherein the vibratory element 104 is at least partially immersed in the fluid being measured. The vibratory element 104 includes a housing 105 that can be affixed to another structure, such as a pipe, conduit, tank, receptacle, manifold, or any other fluid-handling structure. The housing 105 retains the vibratory element 104 while the vibratory element 104 remains at least partially exposed. The vibratory element 104 is therefore configured to be immersed in the fluid.

The vibratory element 104 in the embodiment shown includes first and second tines 112 and 114 that are configured to extend at least partially into the fluid. The first and second tines 112 and 114 comprise elongated elements that may have any desired cross-sectional shape. The first and second tines 112 and 114 may be at least partially flexible or resilient in nature. The vibratory sensor 5 further includes corresponding first and second piezo elements 122 and 124 that comprise piezo-electric crystal elements. The first and second piezo elements 122 and 124 are located adjacent to the first and second tines 112 and 114, respectively. The first and second piezo elements 122 and 124 are configured to contact and mechanically interact with the first and second tines 112 and 114.

The first piezo element 122 is in contact with at least a portion of the first tine 112. The first piezo element 122 is also electrically coupled to the driver circuit 138. The driver circuit 138 provides the generated drive signal to the first piezo element 122. The first piezo element 122 expands and contracts when subjected to the generated drive signal. As a result, the first piezo element 122 may alternatingly deform and displace the first tine 112 from side to side in a vibratory motion (see dashed lines), disturbing the fluid in a periodic, reciprocating manner.

The second piezo element 124 is shown as coupled to a receiver circuit 134 that produces the vibration signal corresponding to the deformations of the second tine 114 in the fluid. Movement of the second tine 114 causes a corresponding electrical vibration signal to be generated by the second piezo element 124. The second piezo element 124 transmits the vibration signal to the meter electronics 20. The meter electronics 20 includes the interface circuit 136. The interface circuit 136 can be configured to communicate with external devices. The interface circuit 136 communicates a vibration measurement signal or signals and may communicate determined fluid characteristics to one or more external devices. The meter electronics 20 can transmit vibration signal characteristics via the interface circuit 136, such as a vibration signal frequency and a vibration signal amplitude of the vibration signal. The meter electronics 20 may transmit fluid measurements via the interface circuit 136, such as a density and/or viscosity of the fluid, among other things. Other fluid measurements are contemplated and are within the scope of the description and claims. In addition, the interface circuit 136 may receive communications from external devices, including commands and data for generating measurement values, for example. In some embodiments, the receiver circuit 134 is coupled to the driver circuit 138, with the receiver circuit 134 providing the vibration signal to the driver circuit 138.

The driver circuit 138 generates the drive signal for the vibratory element 104. The driver circuit 138 can modify characteristics of the generated drive signal. The vibratory element 104 is generally maintained at a resonant frequency, as influenced by the surrounding fluid. The driver circuit 138 includes an open-loop drive 147. The open-loop drive 147 may be used by the driver circuit 138 to generate the drive signal and supply the generated drive signal to the vibratory element 104 (e.g., to the first piezo element 122). In some embodiments, the open-loop drive 147 generates the drive signal to achieve a target phase difference $\phi_t$, commencing at an initial frequency $\omega_o$. The open-loop drive 147 does not operate based on feedback from the vibration signal. The open-loop drive 147 can therefore provide the generated drive signal free of noise and without a time delay due to filtering the vibration signal, as will be described in more detail in the following.

Figure 4:
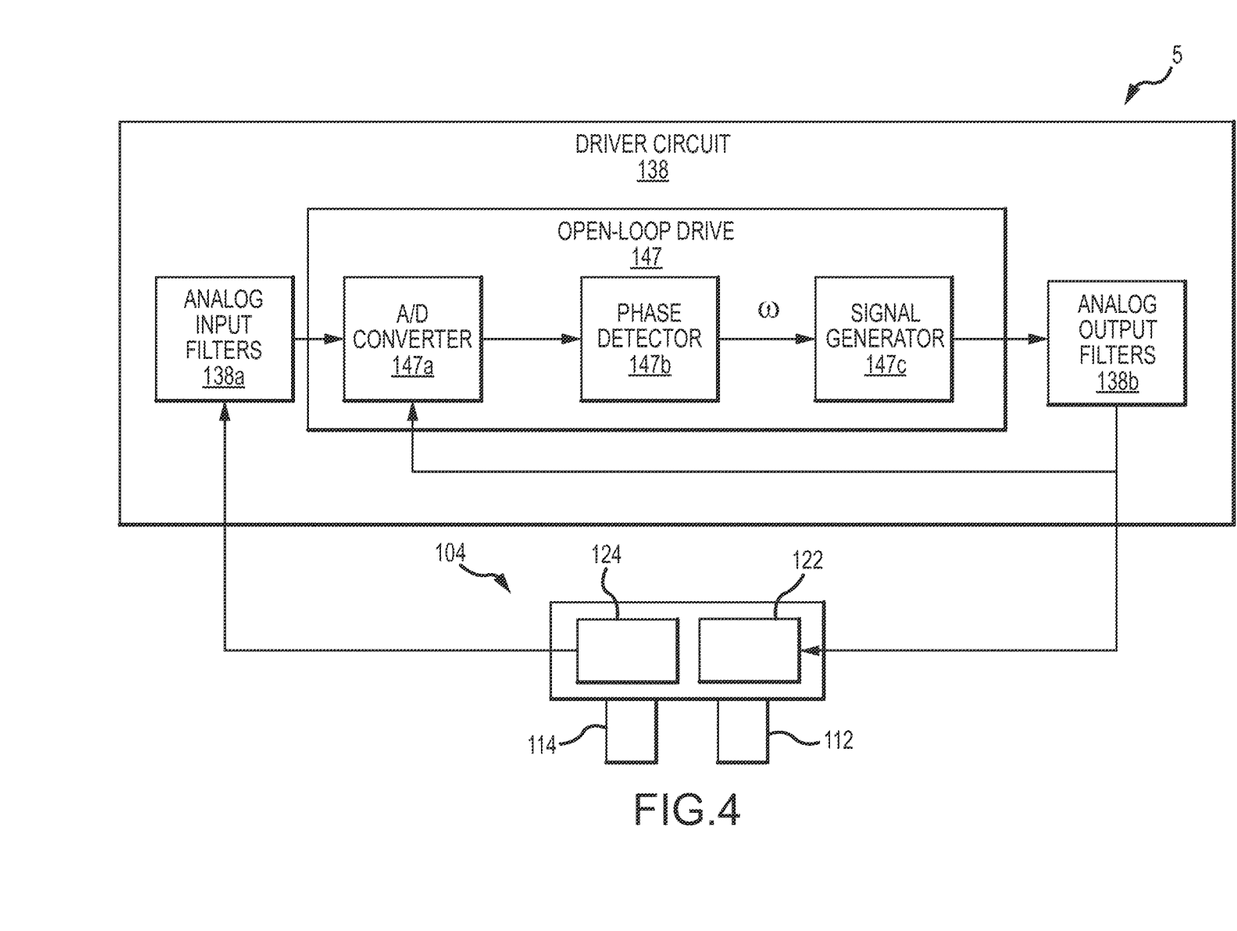
FIG. 4 shows a block diagram of the vibratory sensor 5 with a more detailed representation of the driver circuit 138.

FIG. 4 shows a block diagram of the vibratory sensor 5 with a more detailed representation of the driver circuit 138. The vibratory sensor 5 is shown with the driver circuit 138. The receiver circuit 134 and the interface circuit 136 are not shown for clarity. The driver circuit 138 includes an analog input filter 138a and an analog output filter 138b that are coupled to the open-loop drive 147. The analog input filter 138a filters the vibration signal and the analog output filter 138b filters the generated drive signal.

The open-loop drive 147 includes an analog to digital converter 147a that is coupled to a phase detector 147b. The phase detector 147b is coupled to a signal generator 147c. Also shown is the vibratory element 104, which includes the first piezo element 122 and the second piezo element 124. The open-loop drive 147 can be implemented with a digital signal processor that is configured to execute one or more codes or programs that sample, process, and generate signals. Additionally or alternatively, the open-loop drive 147 can be implemented with an electronics circuit coupled to the digital signal processor or the like.

The vibration signal provided by the first piezo element 122 is sent to the analog input filters 138a. The analog input filters 138a filters the vibration signal prior to the vibration signal being sampled by the analog to digital converter 147a. In the embodiment shown, the analog input filters 138a can be comprised of a low pass filter with cutoff frequency that is about half the sample rate of the open-loop drive 147 although any suitable low pass filter can be employed. The low pass filter can be provided by passive components such as an inductor, a capacitor, and a resistor although any suitable components, distributed or discrete, such as an operational amplifier filter, can be employed.

The analog to digital converter 147a can sample the filtered vibration signal to form a sampled vibration signal. The analog to digital converter 147a can also sample the generated drive signal through a second channel. The sampling can be by any appropriate sampling method. As can be appreciated, the generated drive signal sampled by the analog to digital converter 147a does not have noise associated with the vibration signal. The generated drive signal is provided to the phase detector 147b.

The phase detector 147b can compare the phases of the sampled vibration and generated drive signal. The phase detector 147b can be a processor configured to execute one or more codes or programs that sample, process, and generate signals to detect a phase difference between two signals, as will be described in more detail in the following with reference to FIG. 5. Still referring to the embodiment of FIG. 4, the comparison provides a measured phase difference $\phi_m$ between the sampled vibration signal and the sampled generated drive signal.

The measured phase difference $\phi_m$ is compared with the target phase difference $\phi_t$. The target phase difference $\phi_t$ is a desired phase difference between the vibration signal and the generated drive signal. In an embodiment where the target phase difference $\phi_t$ is approximately 45°, the difference between the measured phase difference $\phi_m$ and the target phase difference $\phi_t$ can be zero if the measured phase difference $\phi_m$ is also the same as or about 45°. However, any appropriate target phase difference $\phi_t$ can be employed in alternative embodiments. Using the comparison between the measured phase difference $\phi_m$ and the target phase difference $\phi_t$, the phase detector 147b can generate a command frequency $\omega$.

The command frequency $\omega$ can be employed to generate the drive signal. Additionally or alternatively, an initial frequency $\omega_o$ that is not determined from the comparison between the measured phase difference $\phi_m$ and the target phase difference $\phi_t$ can be employed. The initial frequency $\omega_o$ could be a preselected frequency used to form an initial generated drive signal. The initial generated drive signal can be sampled as described in the foregoing and compared with the sampled vibration signal. The comparison between the sampled initial generated drive signal and the sampled vibration signal can be used to generate the command frequency $\omega$. The command frequency $\omega$ and the initial frequency $\omega_o$ can have units of radians per second although any suitable units can be employed. The command frequency $\omega$ or the initial frequency $\omega_o$ can be provided to the signal generator 147c.

The signal generator 147c can receive the command frequency $\omega$ from the phase detector 147b and provide the generated drive signal with a frequency that is the same as the command frequency $\omega$. The generated drive signal is sent, as discussed in the foregoing, to the analog to digital converter 147a. The generated drive signal is also sent to the second piezo element 124 via the analog output filter 138b. Additionally or alternatively, the generated drive signal can be sent to other components in other embodiments. In these and other embodiments, the generated drive signal can therefore be determined from the difference between the measured phase difference $\phi_m$ and the target phase difference $\phi_t$, as will be described in more detail in the following.

Figure 5:
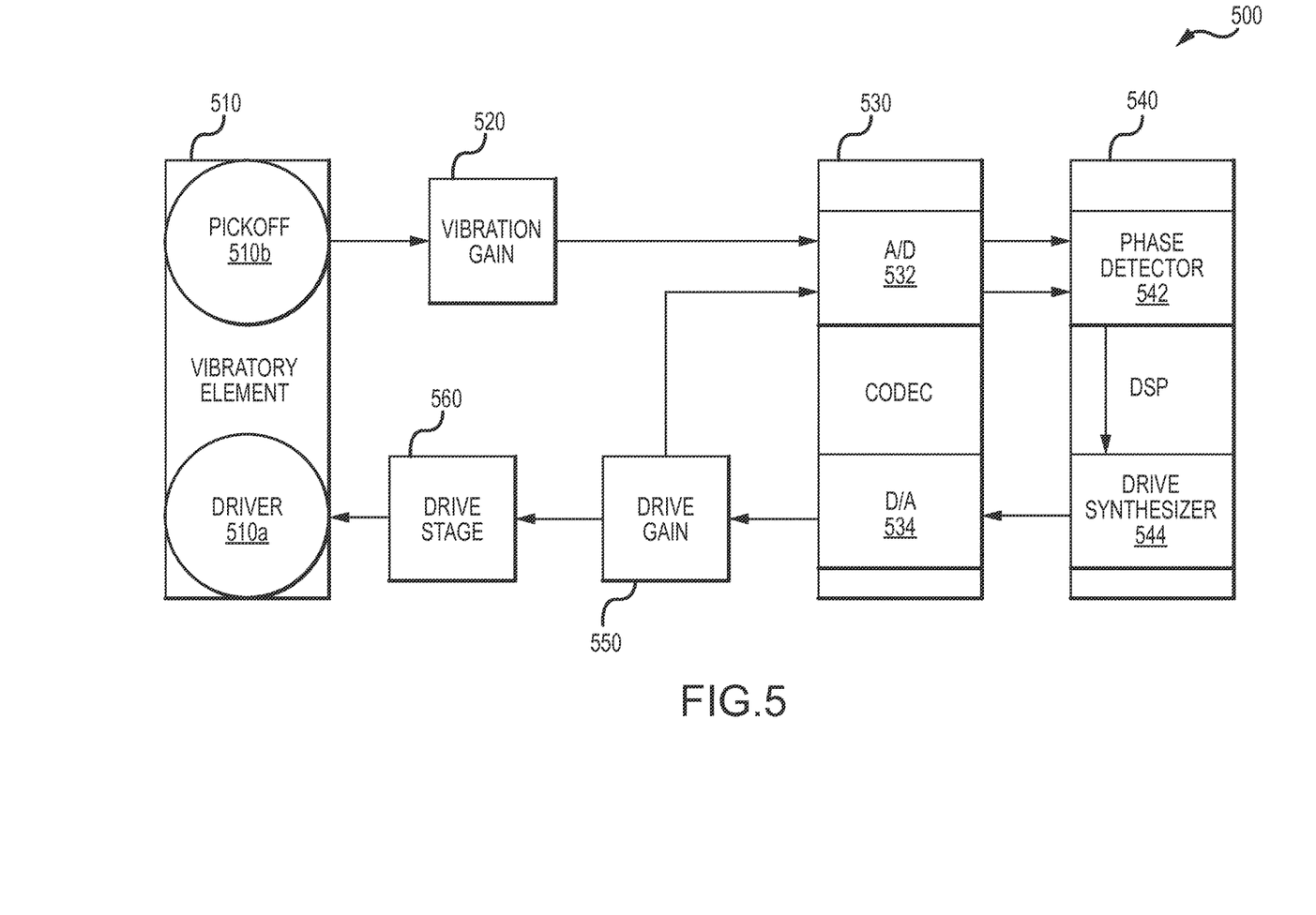
FIG. 5 shows a block diagram 500 of the vibratory sensor 5 according to an embodiment.

FIG. 5 shows a block diagram 500 of the vibratory sensor 5 according to an embodiment. The block diagram 500 includes a vibratory element 510. The vibratory element 510 includes a driver 510a and a pickoff 510b. The block diagram 500 also includes a vibration gain 520 that is coupled to the pickoff 510b. The vibration gain 520 is coupled to an analog to digital converter 532 that is in a codec block 530. The analog to digital converter 532 is coupled to a phase detector 542 in a digital signal processor (DSP) block 540. The DSP block 540 also includes a drive synthesizer 544 that receives a signal from the phase detector 542. The drive synthesizer 544 is coupled to a digital to analog converter 534 that is coupled to a drive gain 550. The drive gain 550 is coupled to a drive stage 560 and the analog to digital converter 532. The drive gain 550 can amplify the generated drive signal provided by the codec block 530.

The codec block 530 is shown as a two-way converter although any suitable configurations can be employed. As shown, the analog to digital converter 532 in the codec block 530 receives a vibration signal from the vibration gain 520. In alternative embodiments, the vibration signal can be provided to the analog to digital converter 532 directly from the pickoff 510b. The analog to digital converter 532 samples the vibration signal, which may be a continuous time signal, with a sampling rate and resolution to generate the sampled vibration signal. The analog to digital converter 532 can include an anti-aliasing filter that removes undesired frequency components from the vibration signal prior to sampling.

The analog to digital converter 532 also samples the generated drive signal provided by the drive gain 550. The generated drive signal from the drive gain 550 can be a continuous time signal although any suitable signal can be provided. Similar to the vibration signal, the analog to digital converter 532 can sample the generated drive signal with an appropriate sampling rate and resolution. The analog to digital converter 532 can also include an anti-aliasing filter that removes any undesired frequency components from the generated drive signal prior to sampling. The sampled vibration and the sampled generated drive signals are provided to the phase detector 542 in the DSP block 540. The phase detector 542 compares the sampled vibration signal with the sampled generated drive signal to determine the measured phase difference $\phi_m$, as will be described in the following.

In the embodiment shown, the phase detector 542 can determine the measured phase difference $\phi_m$ between the sampled vibration and the sampled generated drive signals by correlating the sampled signals. For example, one or more codes or programs that sample, process, and generate signals can implement a transform, along with decimation and other DSP functions, to determine the measured phase difference $\phi_m$. These and other embodiments can be illustrated with the following equations.

The generated drive signal and the vibration signal can be represented in the complex plane by the following equations [1] and [2].

$$z_{gds}(k) = \frac{A}{2}[\exp(j\varphi_{gds}) + \exp(-j(2\omega k + \varphi_{gds}))] \quad [1]$$

$$z_{vs}(k) = \frac{A}{2}[\exp(j\varphi_{vs}) + \exp(-j(2\omega k + \varphi_{vs}))] \quad [2]$$

The $z_{gds}(k)$ function is a complex representation of the generated drive signal and the $z_{vs}(k)$ function is a complex representation of the vibration signal. The $\exp(j(2\omega k+\varphi_{vs}))$ term includes k integer multiples of the frequency w and represents frequency components. Decimation or other filtering can be used to eliminate the frequency components. Accordingly, the complex representations, without the frequency components, can be written as equations [3] and [4]

$$z_{gds}(k) = \frac{A}{2}[\exp(j\varphi_{gds})] \quad [3]$$

$$z_{vs}(k) = \frac{A}{2}[\exp(j\varphi_{vs})]. \quad [4]$$

Performing a complex conjugation and a correlation (e.g., multiplication) on the foregoing equations [3] and [4] results in equation [5] shown below.

$$q(k) = \frac{A^2}{4}e^{-j(\varphi_{gds}-\varphi_{vs})} \quad [5]$$

It can be appreciated that one of the functions is not conjugated (e.g., non-conjugated). From equation [5], the measured phase difference $\phi_m$ between the generated drive signal and the vibration signal can be $$\varphi_m(k)=\arg(q(k))=\varphi_{gds}-\varphi_{vs}. \quad [6]$$

The foregoing illustrates an exemplary embodiment showing how the measured phase difference $\phi_m$ can be determined. As can be appreciated, different embodiments of the phase detector 542 can determine the measured phase difference $\phi_m$ between the sampled vibration signal and the sampled generated drive signal. The measured phase difference $\phi_m$ can be used to determine the command frequency ω, as will be explained in more detail in the following with reference to FIG. 6. Still referring to FIG. 5, the command frequency ω is provided to the drive synthesizer 544.

The drive synthesizer 544 can be a processor that executes one or more codes or programs that receive the command frequency ω and provides a synthesized drive signal. The synthesized drive signal can be a discrete representation of a simple sinusoidal signal. For example, the synthesized drive signal can be an impulse train with an envelope that corresponds to the simple sinusoidal signal. Additionally or alternatively, the drive synthesizer 544 can be a digital circuit, field programmable gate array (FPGA), or the like. For example, the digital circuit could receive a direct current (DC) voltage signal with a magnitude that corresponds to the command frequency ω. In an alternative embodiment, the drive synthesizer could receive a voltage signal (e.g., direct current, etc.) and provide the generated drive signal with the command frequency ω being proportional to the voltage signal.

In the embodiment shown, the drive synthesizer 544 provides the synthesized drive signal to the digital to analog converter 534. The digital to analog converter 534 converts the synthesized drive signal to the generated drive signal. The digital to analog converter 534 can be a zero-order hold that converts, for example, the impulse train into a stepped sinusoidal waveform, although any suitable digital to analog converter 534 can be employed. In alternative embodiments, such as embodiments where the drive synthesizer 544 is the digital circuit or FPGA described in the foregoing, the digital to analog converter 534 may not be needed. In such embodiments, the generated drive signal can be provided without a digital to analog conversion. In these and other embodiments, the generated drive signal can be a simple sinusoidal signal at or about the command frequency ω. In alternative embodiments, the generated drive signal can be comprised of more than one frequency components. In the embodiment shown, the generated drive signal is sent to the drive gain 550.

The drive gain 550 amplifies the generated drive signal and provides the amplified generated drive signal to the analog to digital converter 532 and the drive stage 560. The drive gain 550 and the drive stage 560 can modify the generated drive signal to achieve a desired waveform. For example, the drive gain 550 can amplify the generated drive signal to exceed the power available to the driver 510a. Accordingly, in embodiments where the generated drive signal is the continuous time sinusoidal signal, the generated drive signal provided to the driver 510a can have a trapezoidal shape. Additionally or alternatively, the generated drive signal can have other shapes such as triangle waveform, a chain of different waveforms, or the like. These and other waveforms can be formed using the command frequency ω determined from the measured phase difference $\phi_m$ as will be explained in more detail in the following.

Figure 6:
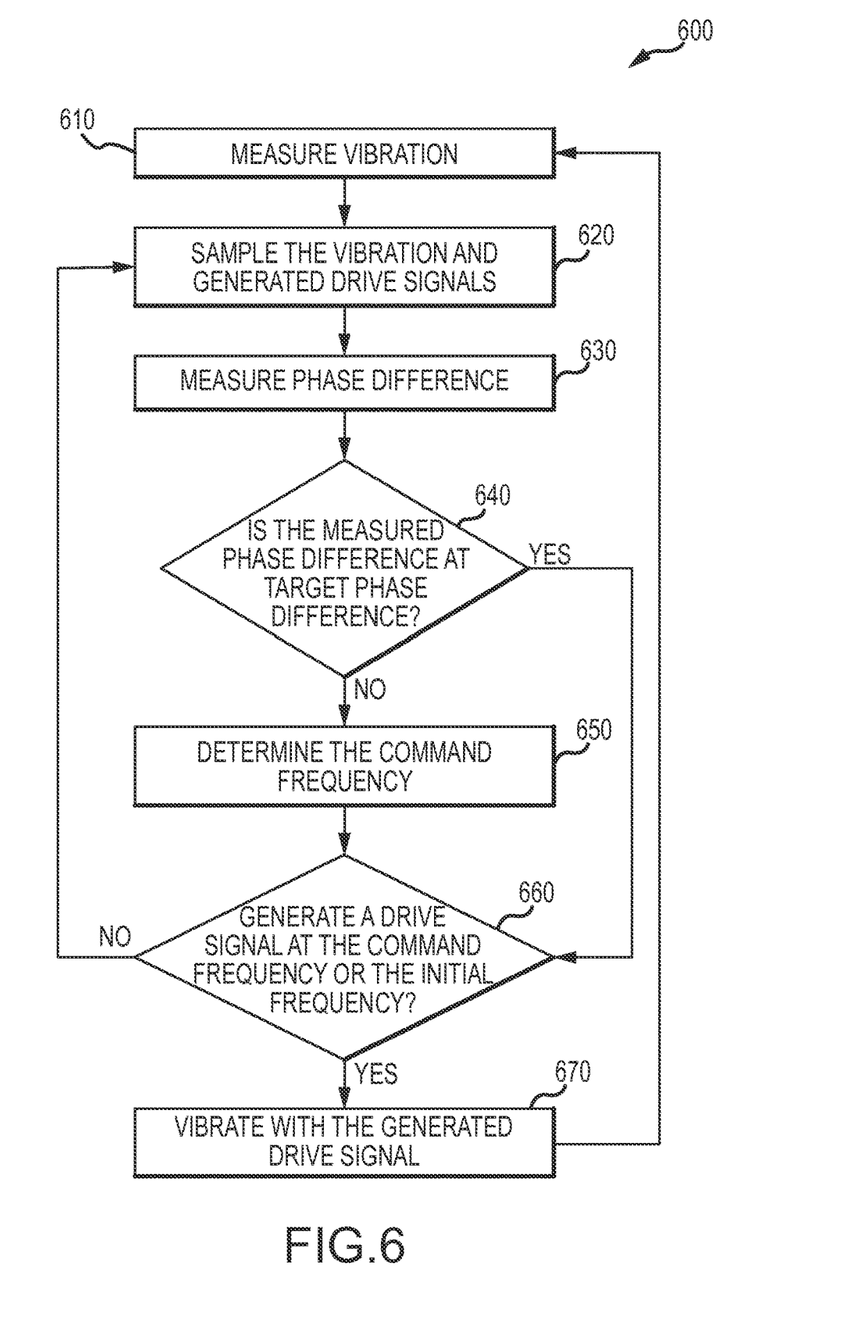
FIG. 6 shows a method 600 of generating the drive signal according to an embodiment.

FIG. 6 shows a method 600 of generating the drive signal according to an embodiment. The method 600 begins with step 610. In step 610, the vibration is measured by the second tine 114. The second tine 114 vibrates due to vibrations in the fluid. The vibrations may be present in the fluid due to the first tine 112 vibrating at the command frequency ω or the initial frequency $\omega_o$. The second piezo element 124 sends the vibration signal to the analog input filters 138a. The analog input filters 138a filters the vibration signal to remove noise and to limit the bandwidth of the vibration signal. The filtered vibration signal is sent to the analog to digital converter 147a, 532. The generated drive signal from the signal generator 147c is also sent to the analog to digital converter 147a, 532.

In step 620, the vibration and generated drive signals are sampled by the analog to digital converter 147a, 532. The sampling can be any appropriate sampling method that converts the vibration signal and generated drive signal into a sequence of numbers, which may be in, for example, binary format. The sampling can be done at any appropriate sampling rate and bit resolution.

In step 630, the measured phase difference $\phi_m$ between the phase of the sampled vibration signal and the phase of the sampled generated drive signal is determined by the phase detector 147b. Although the measured phase difference $\phi_m$ is an angle with units of degrees, other units, such as radians, can be employed in other embodiments. Alternatively, a time difference can be employed rather than the phase difference.

In step 640, the measured phase difference $\phi_m$ is compared with the target phase difference $\phi_t$. In the embodiments described in the foregoing, the target phase difference $\phi_t$ is 45°. If the comparison indicates that the measured phase difference $\phi_m$ is the same as the target phase difference $\phi_t$, then the method 600 continues generating the drive signal at the same command frequency $\omega$ or initial frequency $\omega_o$ in step 660. If the measured phase difference $\phi_m$ is not the same as the target phase difference $\phi_t$, then the command frequency $\omega$ is determined in step 650.

In step 650, the command frequency $\omega$ can be determined from the measured phase difference $\phi_m$. For example, in the embodiments described in the foregoing, if the measured phase difference $\phi_m$ is less than the target phase difference $\phi_t$, then the command frequency $\omega$ is increased. If the measured phased difference $\phi_m$ is greater than the target phase difference $\phi_t$ then the command frequency is decreased. However, in alternative embodiments, the command frequency $\omega$ can be determined from the measured phase difference $\phi_m$ with alternative means. In these and other embodiments, the command frequency $\omega$ is used to generate the drive signal in step 660.

In step 660, the signal generator 147c forms the generated drive signal at the command frequency $\omega$. In an embodiment, the signal generator 147c is comprised of the drive synthesizer 544 and the digital to analog converter 534. Alternatively, the signal generator 147c can be comprised of a digital circuit, FPGA, or the like. In the embodiment described with reference to FIG. 5, the generated drive signal is formed from the synthesized drive signal provided by the drive synthesizer 544. In these and other embodiments, the generated drive signal can be a sinusoidal drive signal with a single frequency although any other appropriate signal or signals can be provided.

The generated drive signal is used to vibrate the vibratory element 104, 510. As shown in FIG. 5, the generated drive signal is provided to the drive gain 550 and the drive stage 560. The drive gain 550 and drive stage 560 modify and provide the generated drive signal to the driver 510a. However, the generated drive signal can be provided to the vibratory element 104, 510 through other means. For example, the generated drive signal can be provided directly to the driver 510a. The generated drive signal can also be sampled and measured. For example, as shown in FIG. 6, step 660 also returns the generated drive signal to step 620, where the generated drive signal is sampled.

In operation, the phase detector 147b can send the command frequency $\omega$ to the signal generator 147c. In some embodiments, the driver circuit 138 vibrates the vibratory element 104 (e.g., the first tine 112, the driver 510a, etc.) at a command frequency $\omega$ and in an open-loop manner to achieve the target phase difference $\phi_t$. The target phase difference $\phi_t$ can be 45° to accurately measure the density of the fluid. However, in alternative embodiments, the target phase difference $\phi_t$ can be another value.

The method 600 and vibratory sensor 5 can provide the generated drive signal. For example, the generated drive signal can be provided by the signal generator 147c at the command frequency $\omega$. In an embodiment, the signal generator 147c can be comprised of the drive synthesizer 544 and the digital to analog converter 534. The command frequency $\omega$ can be determined from the measured phase difference $\phi_m$ between vibration signal and the generated drive signal. The measured phase difference $\phi_m$ can be determined using the phase detector 147b, 542.

As can be appreciated, the frequency of the vibration signal is not measured or compared with the frequency of the generated drive signal. Instead, the phase of the vibration signal and the generated drive signal can be determined using one or more codes or programs that sample, process, and generate signals. For example, according to an embodiment described in the foregoing, the sampled vibration signal and the sampled drive signal are conjugated and correlated, without frequency components, to determine the measured phase difference $\phi_m$. Accordingly, the measured phase difference $\phi_m$ between the vibration signal and the generated drive signal can be determined without the delays associated with the prior art vibratory meters. In addition, the signal generator 147c can provide the generated drive signal free of noise associated with the vibration signal. For example, as described in the foregoing embodiments, the phase detector 542 removes frequency components of the sampled vibration signal and generated drive signal prior to determining the measured phase difference $\phi_m$.

Accordingly, the generated drive signal does not include the noise from the vibration signal or time delay associated with the prior art. Because the generated drive signal is free of the noise associated with the vibration signal, the density measurement is more accurate. In addition, since there is no time delay associated with the prior art filtering, the generated drive signal is more stable. These and other benefits can be obtained with the method 600 and the vibratory sensor 5, as well as alternative embodiments.

The detailed descriptions of the above embodiments are not exhaustive descriptions of all embodiments contemplated by the inventors to be within the scope of the present description. Indeed, persons skilled in the art will recognize that certain elements of the above-described embodiments may variously be combined or eliminated to create further embodiments, and such further embodiments fall within the scope and teachings of the present description. It will also be apparent to those of ordinary skill in the art that the above-described embodiments may be combined in whole or in part to create additional embodiments within the scope and teachings of the present description.

Thus, although specific embodiments are described herein for illustrative purposes, various equivalent modifications are possible within the scope of the present description, as those skilled in the relevant art will recognize. The teachings provided herein can be applied to other methods for generating a drive signal for a vibratory sensor, and not just to the embodiments described above and shown in the accompanying figures. Accordingly, the scope of the embodiments described above should be determined from the following claims.

We claim:

1. A method (600) of generating a drive signal for a vibratory sensor (5), the method comprising:
    vibrating a vibratory element (104, 510) configured to provide a vibration signal;
    receiving the vibration signal from the vibratory element (104, 510) with a receiver circuit (134);

generating the drive signal that vibrates the vibratory element (104, 510) with a driver circuit (138) coupled to the receiver circuit (134) and the vibratory element (104, 510);
comparing a phase of the generated drive signal with a phase of the vibration signal; and
generating a command frequency ω from the comparison of the phase of the generated drive signal and the phase of the vibration signal;
wherein the drive signal is generated at the command frequency ω by an open-loop drive (147) in the driver circuit (138).

2. The method (600) of claim 1, wherein the comparing the phase of the generated drive signal with the phase of the vibration signal comprises comparing a sampled generated drive signal with a sampled vibration signal.

3. The method (600) of claim 2, further comprising removing at least one frequency component from the at least one of the sampled generated drive signal and the sampled vibration signal.

4. The method (600) of claim 2, wherein the comparing the sampled generated drive signal with the sampled vibration signal comprises performing a correlation of the sampled generated drive signal and the sampled vibration signal.

5. The method (600) of claim 2, wherein the comparing the sampled generated drive signal with the sampled vibration signal comprises:
conjugating one of the sampled generated drive signal and the sampled vibration signal; and
multiplying the conjugated one of the sampled generated drive signal and the sampled vibration signal with the non-conjugated one of the sampled generated drive signal and the sampled vibration signal.

6. The method (600) of claim 1, wherein the comparing the phase of the generated drive signal with the phase of the vibration signal comprises:
determining a measured phase difference $\phi_m$ between the phase of the generated drive signal and the phase of the vibration signal; and
comparing the measured phase difference $\phi_m$ with a target phase difference $\phi_t$ to determine if the measured phase difference $\phi_m$ is at the target phase difference $\phi_t$.

7. The method (600) of claim 6, further comprising measuring a density of a fluid when the measured phase difference $\phi_m$ is at the target phase difference $\phi_t$.

8. The method (600) of claim 1, further comprising:
providing the command frequency ω to a signal generator (147c); and
generating the drive signal at the command frequency ω with the signal generator (147c).

9. The method (600) of claim 8, wherein the generating the drive signal at the command frequency ω with the signal generator (147c) comprises:
forming a synthesized drive signal with a drive synthesizer (544); and
converting the synthesized drive signal to the generated drive signal with a digital to analog converter (534).

10. A vibratory sensor (5), comprising:
a vibratory element (104, 510) configured to provide a vibration signal;
a receiver circuit (134) that receives the vibration signal from the vibratory element (104); and
a driver circuit (138) coupled to the receiver circuit (134) and the vibratory element (104), the driver circuit (138) configured to:
generate a drive signal that vibrates the vibratory element (104, 510);
compare a phase of the generated drive signal with a phase of the vibration signal; and
determine a command frequency co from the comparison of the phase of the generated drive signal and the phase of the vibration signal;
wherein the drive signal is generated at the command frequency ω by an open-loop drive (147) in the driver circuit (138).

11. The vibratory sensor (5) of claim 10, the driver circuit (138) being configured to compare a sampled generated drive signal with a sampled vibration signal.

12. The vibratory sensor (5) of claim 11, wherein the driver circuit (138) is further configured to remove at least one frequency component from at least one of the sampled generated drive signal and the sampled vibration signal.

13. The vibratory sensor (5) of claim 11, wherein the driver circuit (138) is further configured to perform a correlation of the sampled generated drive signal and the sampled vibration signal.

14. The vibratory sensor (5) of claim 11, wherein the driver circuit (138) is further configured to:
conjugate one of the sampled generated drive signal and the sampled vibration signal; and
multiplies the conjugated one of the sampled generated drive signal and the sampled vibration signal with the non-conjugated one of the sampled generated drive signal and the sampled vibration signal.

15. The vibratory sensor (5) of claim 10, wherein the driver circuit (138) is comprised of a phase detector (147b, 542) configured to:
determine a measured phase difference $\phi_m$ between the phase of the generated drive signal and the phase of the vibration signal; and
compare the measured phase difference $\phi_m$ with a target phase difference $\phi_t$ to determine if the measured phase difference $\phi_m$ is at the target phase difference $\phi_t$.

16. The vibratory sensor (5) of claim 15, wherein the driver circuit (138) is further configured to measure the density of the fluid when the measured phase difference $\phi_m$ is at the target phase difference $\phi_t$.

17. The vibratory sensor (5) of claim 10, wherein the driver circuit (138) is comprised of:
a phase detector (147b, 542) and a signal generator (147c) wherein:
the phase detector (147b) is configured to determine the command frequency ω from the comparison of the phase of the generated drive signal and the phase of the vibration signal and provides the command frequency ω to a signal generator (147c); and
the signal generator (147c) configured to generate the drive signal at the command frequency ω.

18. The vibratory sensor (5) of claim 17, wherein the signal generator (147c) comprises:
a drive synthesizer (544) configured to form a synthesized drive signal; and
a digital to analog converter (534) configured to convert the synthesized drive signal to the generated drive signal.

* * * * *

UNITED STATES PATENT AND TRADEMARK OFFICE
CERTIFICATE OF CORRECTION

Page 1 of 1

PATENT NO. : 10,168,264 B2
APPLICATION NO. : 14/781259
DATED : January 1, 2019
INVENTOR(S) : Craig B McAnally and Andrew S. Kravitz It is certified that error appears in the above-identified patent and that said Letters Patent is hereby corrected as shown below:

In the Specification

Column 9, Line 34 replace that portion of the formula reading "exp(j(2ωk+" with --exp(-j(2ωk+--

Column 9, Line 35 replace "wand" with --ω and--

In the Claims

Column 14, Line 8 replace "frequency co" with --frequency ω--

Signed and Sealed this
Tenth Day of December, 2019

Andrei Iancu
*Director of the United States Patent and Trademark Office*